United States Patent
Papkovsky et al.

(10) Patent No.: US 9,945,778 B2
(45) Date of Patent: Apr. 17, 2018

(54) INDIVIDUALLY AND FLEXIBLY DEPLOYABLE TARGET-ANALYTE SENSITIVE PARTICULATE PROBES AND METHOD OF MAKING AND USING

(71) Applicant: LUXCEL BIOSCIENCES, LTD, Cork (IE)

(72) Inventors: Dmitri Boris Papkovsky, Blarney (IE); James Nial Hynes, Ovens (IE); Richard Fernandes, Newbridge (IE)

(73) Assignee: LUXCEL BIOSCIENCES, LTD, Cork (IE)

( * ) Notice: Subject to any disclaimer, the term of this patent is extended or adjusted under 35 U.S.C. 154(b) by 0 days.

(21) Appl. No.: 14/649,011

(22) PCT Filed: Dec. 5, 2012

(86) PCT No.: PCT/EP2012/074551
§ 371 (c)(1),
(2) Date: Jun. 2, 2015

(87) PCT Pub. No.: WO2014/086411
PCT Pub. Date: Jun. 12, 2014

(65) Prior Publication Data
US 2015/0308953 A1    Oct. 29, 2015

(51) Int. Cl.
*G01N 21/64*   (2006.01)
*G01N 21/77*   (2006.01)
(Continued)

(52) U.S. Cl.
CPC ......... *G01N 21/64* (2013.01); *G01N 21/643* (2013.01); *G01N 21/6408* (2013.01);
(Continued)

(58) Field of Classification Search
CPC ...... G01N 21/64; G01N 21/643; G01N 21/63; G01N 21/6408; G01N 21/21862;
(Continued)

(56) References Cited

U.S. PATENT DOCUMENTS 4,476,870 A    10/1984  Paterson et al.
4,652,143 A    3/1987   Wickersheim et al.
(Continued)

FOREIGN PATENT DOCUMENTS

EP    0131404 A2    1/1985
EP    1134583 A1    9/2001
(Continued)

OTHER PUBLICATIONS

Papkovsky D B et al, Biosensors on the basis of luminescent oxygen sensor: the use of microporous light-scattering support materials, 1998, Sensor and Actuators B, 51, 137-145.*

*Primary Examiner* — Christine T Mui
(74) *Attorney, Agent, or Firm* — Sherrill Law Offices, PLLC (57) ABSTRACT

Flexibly deployable, discrete, target-analyte sensitive particulate probes and methods of manufacturing and using. The probes each comprise a porous scaffold particle coated with an optically-active, target-analyte sensitive material. The scaffold particle has at least one of (i) a volume of 0.5 to 500 mm³, and (ii) a largest dimension of 2 to 20 mm.

14 Claims, 3 Drawing Sheets

(51) Int. Cl.
*G01N 21/63* (2006.01)
*G01N 21/75* (2006.01)

(52) U.S. Cl.
CPC ..... *G01N 21/77* (2013.01); *G01N 2021/6432* (2013.01); *G01N 2201/061* (2013.01); *G01N 2201/12* (2013.01)

(58) Field of Classification Search
CPC ...... G01N 21/636; G01N 21/77; G01N 21/75; G01N 21/862
USPC .................................. 436/172, 164
See application file for complete search history.

(56) References Cited

U.S. PATENT DOCUMENTS

| | | | |
|---|---|---|---|
| 4,810,655 A | 3/1989 | Khalil et al. |
| 4,965,087 A | 10/1990 | Wolfbeis et al. |
| 5,030,420 A | 7/1991 | Bacon et al. |
| 5,094,959 A | 3/1992 | Allen et al. |
| 5,114,676 A | 5/1992 | Leiner et al. |
| 5,407,892 A | 4/1995 | Murakami et al. |
| 5,462,879 A | 10/1995 | Bentsen |
| 5,567,598 A | 10/1996 | Sitt et al. |
| 5,595,708 A | 1/1997 | Berndt |
| 5,718,842 A | 2/1998 | Papkovsky et al. |
| 5,863,460 A | 1/1999 | Slovacek et al. |
| 5,885,843 A | 3/1999 | Ayers et al. |
| 6,331,438 B1 * | 12/2001 | Aylott .................... G01N 21/66 422/82.07 |
| 6,379,969 B1 | 4/2002 | Mauze et al. |
| 6,395,506 B1 | 5/2002 | Pitner et al. |
| 6,689,438 B2 | 2/2004 | Kennedy et al. |
| 6,989,246 B2 | 1/2006 | Yeh |
| 7,045,367 B2 | 5/2006 | Kaganove et al. |
| 7,138,270 B2 | 11/2006 | Papkovsky et al. |
| 7,368,153 B2 | 5/2008 | Barmore et al. |
| 7,470,840 B2 | 12/2008 | Emrick et al. |
| 7,534,615 B2 | 5/2009 | Havens |
| 7,569,395 B2 | 8/2009 | Havens et al. |
| 7,586,106 B2 | 9/2009 | Kleinerman |
| 7,679,745 B2 | 3/2010 | Claps et al. |
| 7,749,768 B2 | 7/2010 | Havens et al. |
| 7,849,729 B2 | 12/2010 | Miller et al. |
| 7,862,770 B2 | 1/2011 | Shahriari |
| 8,084,001 B2 | 12/2011 | Burns et al. |
| 8,158,438 B2 | 4/2012 | Leiner et al. |
| 8,242,162 B2 | 8/2012 | Meador et al. |
| 2001/0018194 A1 | 8/2001 | Terpetschnig et al. |
| 2001/0029049 A1 * | 10/2001 | Walt .................... G01N 21/6428 436/518 |
| 2004/0033575 A1 | 2/2004 | Van Duijn et al. |
| 2005/0037512 A1 | 2/2005 | Yeh et al. |
| 2007/0042412 A1 | 2/2007 | Papkovsky et al. |
| 2008/0051646 A1 | 2/2008 | Papkovsky et al. |
| 2008/0146460 A1 * | 6/2008 | Pollok .................... C12Q 1/37 506/18 |
| 2008/0190172 A1 | 8/2008 | Jones |
| 2008/0199360 A1 | 8/2008 | Shahriari |
| 2009/0028756 A1 * | 1/2009 | Shahriari ........... G01N 21/6408 422/83 |
| 2009/0029402 A1 | 1/2009 | Papkovsky |
| 2001/0136247 | 6/2011 | Papkovsky |
| 2012/0129268 A1 * | 5/2012 | Mayer .................. G01N 21/643 436/138 |

FOREIGN PATENT DOCUMENTS

EP 2455746 A1 11/2011
WO 2008146087 A2 12/2008

* cited by examiner

INDIVIDUALLY AND FLEXIBLY DEPLOYABLE TARGET-ANALYTE SENSITIVE PARTICULATE PROBES AND METHOD OF MAKING AND USING

BACKGROUND

Optically-active, target-analyte sensitive indicator dyes and compounded materials containing such dyes are widely used in the construction of probes and sensors for quantification and monitoring of target-analytes. Such sensors are particularly suited for use in those situations where nondestructive and/or continuous quantification and/or monitoring of a target-analyte within an enclosed space is necessary or desired as such sensors are amenable to repetitive, noninvasive and contactless interrogation through a variety of common barrier materials.

Sensors employing an optically-active, target-analyte sensitive indicator dye commonly immobilize the dye by embedding the dye within a polymer matrix that is permeable to the target-analyte, hereinafter referenced as an optically-active indicator matrix.

To facilitate handling and use, and avoid contamination of the sample being tested, the optically-active indicator matrix is commonly deposited as a solid-state coating, film, layer or dot on an appropriate substrate support material to form autonomously deployable sensors. See for example United States Published Patent Applications 2011/0136247, 2009/0029402, 2008/199360, 2008/190172, 2007/0042412, and 2004/0033575; U.S. Pat. Nos. 8,242,162, 8,158,438, 7,862,770, 7,849,729, 7,749,768, 7,679,745, 7,674,626, 7,569,395, 7,534,615, 7,368,153, 7,138,270, 6,989,246, 6,689,438, 6,395,506, 6,379,969, 6,080,574, 5,885,843, 5,863,460, 5,718,842, 5,595,708, 5,567,598, 5,462,879, 5,407,892, 5,114,676, 5,094,959, 5,030,420, 4,965,087, 4,810,655, and 4,476,870; PCT International Published Application WO 2008/146087; and European Published Patent Application EP 1134583. Such optical sensors are available from a number of suppliers, including Presens Precision Sensing, GmbH of Regensburg, Germany, Oxysense of Dallas, Tex., USA, and Luxcel Biosciences, Ltd of Cork, Ireland.

Due to a prolific increase in the use of such optical sensors, manufacturers have begun to supply assay vessels and packaging films with an integrated optically-active indicator sensor, thereby facilitating use of such sensors by the end user, particularly those who assay large numbers of test samples on a regular basis. Examples of commercially available assay vessels with an integrated optically-active sensor include microtitter plates available from BD Biosciences of Franklin Lakes, N.J., USA and PreSens—Precision Sensing GmbH of Regensberg, Germany; disposable plastic vials available from Mocon of Minneapolis, Minn., USA and Luxcel Biosciences, Ltd. of Cork, Ireland, and culturing flasks available from PreSense.

Such optically active sensors are usually integrated into assay vessels by depositing a solution or suspension of the optically-active indicator matrix directly onto an inner surface of the assay vessel as a polymeric 'cocktail', or adhesively attaching a solid state sensor to an inner surface of the assay vessel.

While constituting a significant advance and finding widespread acceptance within the industry, the manufacture of such sensor-integrated assay vessels is difficult as it requires precision deposition of small aliquots (typically nl and µl quantities) of a viscous cocktail on the inner surface of widely variable and often diminutive assay vessels. Inaccurate or inconsistent size, shape or location of the optically-active indicator matrix, as well as the drying/curing rate of the deposited matrix can result in significant variability in working properties of the resulting sensors. Hence, such sensor-integrated assay vessels are generally expensive to manufacture. Furthermore, use of sensor-integrated assay vessels restricts the end user to use of only those types of assay vessels available with an integrated sensor, thereby reducing the ability to change or adjust experimental conditions in terms of the assay vessel type, size, geometry, alignment, material of construction, etc. Due to high start-up production costs, and strong but limited demand for all but a few types of "sensorized" assay vessels, the industry is unlikely to significantly expand the types of assay vessels available with an integrated sensor.

One alternative for avoiding the drawbacks associated with the deployment of solid-state optically active sensors, is to employ fluid compositions containing the indicator dye in solution or suspension as a liquid or in the form of solid state nano or micro particles which are added to and blended into the samples being tested. This allows the sensor material to be supplied separately from the assay vessels, thereby facilitating a more versatile use relative to the integrated solid state sensors. However, such sensors contaminate the sample and require the use of a much greater quantity of indicator dye as the dye is diluted by the sample.

Accordingly, a substantial need exists for an optically-active, target-analyte sensitive probe capable of quick, easy, flexible and cost effective deployment in a wide variety of assay vessels while consistently and reliably providing sensitive,d accurate and convenient target-analyte measurements.

SUMMARY OF THE INVENTION

A first aspect of the invention is a flexibly deployable, discrete target-analyte sensitive probe. The probe comprises a porous scaffold particle coated with an optically-active, target-analyte sensitive material. The scaffold particle has at least one of (i) a volume of 0.5 to 500 mm$^3$, and (ii) a largest dimension of 2 to 20 mm. In a preferred embodiment the probe has a density of greater than 1.2 g/cm$^3$ so that the probe, when introduced into an assay vessel will remain at or sink to the bottom of the vessel when combined with common test samples.

A second aspect of the invention is an article of commerce comprising a plurality of probes in accordance with the first aspect of the invention retained as a commingled supply of probes within a container from which the probes may be individually and discretely dispensed and used. In a preferred embodiment the probes are microbially sanitized probes.

A third aspect of the invention is a method for measuring concentration of a target-analyte within an enclosed space employing a probe according to the first aspect of the invention. The method includes the steps of (A) obtaining a supply of the target-analyte sensitive probes according to the first aspect of the invention, (B) placing a known number of probes from the supply of probes within a space to form a sensor comprised of at least one probe, (C) enclosing the space, and (D) ascertaining target-analyte concentration within the enclosed space by: (i) exposing the sensor to excitation radiation to create an excited sensor, (ii) measuring radiation emitted by the excited sensor, and (iii) converting the measured emission to a target-analyte concentration based upon a known conversion algorithm.

A fourth aspect of the invention is a method for measuring concentration of a target-analyte within the chamber of a plurality of receptacles employing probes dispensed from the second aspect of the invention. The method includes the steps of (A) obtaining an article of commerce according to the second aspect of the invention, (B) dispensing a first known number of probes from the container, constituting a first fraction of the total number of commingled probes, into a chamber defined by a first receptacle to form a first sensor comprised of at least one probe, (C) dispensing a second known number of probes from the same container, constituting a second fraction of the total number of commingled probes, into the chamber of a second receptacle to form a second sensor comprised of at least one probe, wherein the second receptacle is different than and dissimilar to the first receptacle, (D) enclosing the chamber defined by the first receptacle, (E) enclosing the chamber defined by the second receptacle, (F) ascertaining target-analyte concentration within the enclosed chamber of the first receptacle by: (i) exposing the first sensor to excitation radiation to create an excited first sensor, (ii) measuring radiation emitted by the excited first sensor, and (iii) converting the measured emission to a target-analyte concentration based upon a known conversion algorithm, and (G) ascertaining target-analyte concentration within the enclosed chamber of the second receptacle by: (i) exposing the second sensor to excitation radiation to create an excited second sensor, (ii) measuring radiation emitted by the excited second sensor, and (iii) converting the measured emission to a target-analyte concentration based upon a known conversion algorithm.

A fifth aspect of the invention is a method for monitoring changes in target-analyte concentration within an enclosed space employing a target-analyte sensitive probe according to the first aspect of the invention. The method includes the steps of (A) obtaining a supply of the target-analyte sensitive probes according to the first aspect of the invention, (B) placing a known number of probes from the supply of probes within a space to form a sensor comprised of at least one probe, (C) enclosing the space, (D) ascertaining target-analyte concentration within the enclosed space over time by: (i) taking at least two emission measurements over time, each measurement comprising the steps of: (1) exposing the sensor to excitation radiation to create an excited sensor, and (2) measuring radiation emitted by the excited sensor, (ii) measuring passage of time between at least two of the emission measurements to determine a time interval between identified emission measurement, and (iii) converting at least the identified emission measurements to a target-analyte concentration based upon a known conversion algorithm, and (E) reporting at least one of (i) at least the two ascertained target-analyte concentrations and the time interval between those reported concentrations, and (ii) a rate of change in target-analyte concentration within the enclosed space calculated from data obtained in step (D).

A sixth aspect of the invention is a method for measuring concentration of a target-analyte of interest within an enclosed space employing different target-analyte sensitive probes according to the first aspect of the invention, wherein the target-analyte of interest is selectable from and selectively transitional amongst a plurality of different target-analytes without accessing the space once enclosed. The method includes the steps of (A) obtaining a supply of the target-analyte sensitive probes according to the first aspect of the invention wherein the supply includes probes that are sensitive to different target-analytes and uniquely interrogatable relative to one another, (B) placing at least two of the obtained probes sensitive to different target-analytes within a space, to form a sensor sensitive to at least two different target-analytes, (C) enclosing the space, and (D) ascertaining concentration of a target-analyte of interest within the enclosed space, selected from the at least two different target-analytes to which the at least two placed probes are sensitive, by: (i) exposing the sensor to excitation radiation effective for exciting the probe sensitive to the target-analyte of interest, (ii) measuring radiation emitted by the excited probe sensitive to the target-analyte of interest, and (iii) converting the measured emission to a concentration of the target-analyte of interest based upon a known conversion algorithm.

A seventh aspect of the invention is method for measuring concentration of at least two different target-analytes within an enclosed space employing different target-analyte sensitive probes according to the first aspect of the invention. The method includes the steps of (A) obtaining a first supply of target-analyte sensitive probes according to the first aspect of the invention which are sensitive to a first target-analyte, (B) obtaining a second supply of target-analyte sensitive probes according to the first aspect of the invention which are sensitive to a second target-analyte which is different from the first target-analyte, and wherein the probes sensitive to a first target-analyte and the probes sensitive to a second target-analyte are uniquely interrogatable relative to one another, (C) placing at least one probe from the first supply of probes and at least one probe from the second supply of probes within a space, to form a sensor sensitive to both first and second target-analytes, (D) enclosing the space, (E) ascertaining concentration of the first target-analyte within the enclosed space, by: (i) exposing the sensor to excitation radiation effective for exciting the probe sensitive to the first target-analyte, (ii) measuring radiation emitted by the excited probe sensitive to the first target-analyte, and (iii) converting the measured emission to a concentration of the first target-analyte based upon a known conversion algorithm, and (F) ascertaining concentration of the second target-analyte within the enclosed space, by: (i) exposing the sensor to excitation radiation effective for exciting the probe sensitive to the second target-analyte, (ii) measuring radiation emitted by the excited probe sensitive to the second target-analyte, and (iii) converting the measured emission to a concentration of the second target-analyte based upon a known conversion algorithm.

An eighth aspect of the invention is method for monitoring changes in concentration of at least two different target-analytes within an enclosed space employing different target-analyte sensitive probes according to the first aspect of the invention. The method includes the steps of (A) obtaining a first supply of target-analyte sensitive probes according to the first aspect of the invention which are sensitive to a first target-analyte, (B) obtaining a second supply of target-analyte sensitive probes according to the first aspect of the invention which are sensitive to a second target-analyte which is different from the first target-analyte, and wherein the probes sensitive to a first target-analyte and the probes sensitive to a second target-analyte are uniquely interrogatable relative to one another, (C) placing at least one probe from the first supply of probes and at least one probe from the second supply of probes within a space, to form a sensor sensitive to both first and second target-analytes, (D) enclosing the space, (E) ascertaining concentration of the first target-analyte within the enclosed space, by: (i) taking a first set of at least two emission measurements over time, each measurement comprising the steps of: (1) exposing the sensor to excitation radiation effective for exciting the probe sensitive to the first target-analyte, and (2) measuring radiation emitted by the excited probe sensitive to the first target-analyte, (ii) measuring passage of time between at least two of the first set emission measurements to determine a time interval between identified first set emission measurements, and (iii) converting the measured emission to a concentration of the first target-analyte based upon a known conversion algorithm, and (F) ascertaining concentration of the second target-analyte within the enclosed space, by: (i) taking a second set of at least two emission measurements over time, each measurement comprising the steps of: (1) exposing the sensor to excitation radiation effective for exciting the probe sensitive to the second target-analyte, and (2) measuring radiation emitted by the excited probe sensitive to the second target-analyte, (ii) measuring passage of time between at least two of the second set emission measurements to determine a time interval between identified second set emission measurements, and (iii) converting at least the identified second set emission measurements to a concentration of the second target-analyte based upon a known conversion algorithm, (G) reporting at least one of (i) at least two ascertained first target-analyte concentrations and the time interval between those reported concentrations, and (ii) a rate of change in first target-analyte concentration within the enclosed space calculated from data obtained in step (E), and (H) reporting at least one of (i) at least two ascertained second target-analyte concentrations and the time interval between those reported concentrations, and (ii) a rate of change in second target-analyte concentration within the enclosed space calculated from data obtained in step (F).

A ninth aspect of the invention is a method of manufacturing a probe according to the first aspect of the invention. The method includes the steps of (A) preparing a coating cocktail which contains at least the optically-active target-analyte sensitive material dissolved in a solvent, (B) applying the cocktail to the porous scaffold particle, and (C) allowing the applied cocktail to dry, whereby a solid-state thin film coating of optically-active target-analyte sensitive material is formed on the scaffold particle to form the probe.

In one embodiment of the invention there is provided a flexibly deployable, discrete target-analyte sensitive probe, comprising a porous scaffold particle coated with an optically-active, target-analyte sensitive material, wherein the scaffold particle has at least one of (i) a volume of 0.5 to 500 mm$^3$, and (ii) a largest dimension of 2 to 20 mm.

In one embodiment, the scaffold particle has a volume of 5 to 100 mm$^3$.

In one embodiment, the scaffold particle has a largest dimension of 3 to 10 mm.

In one embodiment, the probe has a density of greater than 1.2 g/cm$^3$.

In one embodiment, the scaffold particle material is porous glass.

In one embodiment, the scaffold particle is translucent to interrogation light.

In one embodiment, the target-analyte sensitive material is a photoluminescent material.

Preferably, the photoluminescent material includes at least a fluorescent or phosphorescent indicator dye having a responsive optical characteristic that changes in response to changes in the concentration or partial pressure of target-analyte to which the dye is exposed.

In one embodiment, (i) the responsive optical characteristic is at least one of photoluminescence lifetime and photoluminescence intensity, and (ii) the indicator dye is sensitive to the partial pressure of oxygen.

In one embodiment, the coating comprises a target-analyte sensitive indicator dye incorporated in a target-analyte permeable polymeric matrix.

Preferably, the target-analyte sensitive indicator dye is an oxygen sensitive photoluminescent transition metal complex selected from the group consisting of a ruthenium bipyridyl, a ruthenium diphenylphenanotroline, a platinum porphyrin, a palladium porphyrin, a phosphorescent complex of a tetrabenzoporphyrin, a chlorin, a porphyrin-ketone, an azaporphyrin and a long-decay luminescent complex of iridium (III) or osmium(II).

Preferably, the polymeric matrix component is selected from the group consisting of silicone, polystrene, polycarbonate, and polysulfone.

In one embodiment of the invention, there is provided an article of commerce, comprising a plurality of probes as described above retained as a commingled supply of probes within a container from which the probes may be individually and discretely dispensed.

In one embodiment concerning the article of commerce, the probes within the container are sanitized probes.

In one embodiment concerning the article of commerce, the probes within the container are sterilized probes.

In one embodiment of the invention, there is provided a method for measuring concentration of a target-analyte within an enclosed space, comprising the steps of:
(a) obtaining a supply of target-analyte sensitive probes as described above,
(b) placing a known number of probes from the supply of probes within a space to form a sensor comprised of at least one probe,
(c) enclosing the space, and
(d) ascertaining target-analyte concentration within the enclosed space by:
  (i) exposing the sensor to excitation radiation to create an excited sensor,
  (ii) measuring radiation emitted by the excited sensor, and
  (iii) converting the measured emission to a target-analyte concentration based upon a known conversion algorithm.

In one embodiment, the space is hermetically enclosed, and the method further comprises the step of placing a liquid test sample into the space prior to hermetically enclosing the space.

Preferably, (i) the space is enclosed within a receptacle, (ii) a single probe is placed within the space, and (ii) the probe is contactlessly interrogated through the receptacle.

More preferably, (i) the space is enclosed within a receptacle having a bottom, (ii) the method further comprises the step of placing a liquid test sample into the space prior to enclosing the space, (iii) the placed probes each have a density greater than the liquid test sample placed into the space, whereby the placed probes sink to the bottom of the receptacle, and (iv) the placed probes are contactlessly interrogated through the bottom of the receptacle.

In one embodiment of the invention, there is provided a method for measuring concentration of a target-analyte within an enclosed space, comprising the steps of:
(a) obtaining an article of commerce as described above,
(b) dispensing a known number of probes from the container, constituting a fraction of the total number of commingled probes, into a space to form a sensor comprised of at least one probe,
(c) enclosing the space, and
(d) ascertaining target-analyte concentration within the enclosed space by:
  (i) exposing the sensor to excitation radiation to create an excited sensor, (ii) measuring radiation emitted by the excited sensor, and
(iii) converting the measured emission to a target-analyte concentration based upon a known conversion algorithm.

In one embodiment of the invention, there is provided a method for measuring concentration of a target-analyte within the chamber of a plurality of receptacles, comprising the steps of:
(a) obtaining an article of commerce as described above,
(b) dispensing a first known number of probes from the container, constituting a first fraction of the total number of commingled probes, into a chamber defined by a first receptacle to form a first sensor comprised of at least one probe,
(c) dispensing a second known number of probes from the same container, constituting a second fraction of the total number of commingled probes, into the chamber of a second receptacle to form a second sensor comprised of at least one probe, wherein the second receptacle is different than and dissimilar to the first receptacle,
(d) enclosing the chamber defined by the first receptacle,
(e) enclosing the chamber defined by the second receptacle,
(f) ascertaining target-analyte concentration within the enclosed chamber of the first receptacle by:
  (i) exposing the first sensor to excitation radiation to create an excited first sensor,
  (ii) measuring radiation emitted by the excited first sensor, and
  (iii) converting the measured emission to a target-analyte concentration based upon a known conversion algorithm, and
(g) ascertaining target-analyte concentration within the enclosed chamber of the second receptacle by:
  (i) exposing the second sensor to excitation radiation to create an excited second sensor,
  (ii) measuring radiation emitted by the excited second sensor, and
  (iii) converting the measured emission to a target-analyte concentration based upon a known conversion algorithm.

In one embodiment of the invention, there is provided a method for monitoring changes in target-analyte concentration within an enclosed space, comprising the steps of:
(a) obtaining a supply of target-analyte sensitive probes as described above,
(b) placing a known number of probes from the supply of probes within a space to form a sensor comprised of at least one probe,
(c) enclosing the space,
(d) ascertaining target-analyte concentration within the enclosed space over time by:
  (i) taking at least two emission measurements over time, each measurement comprising the steps of:
    (1) exposing the sensor to excitation radiation to create an excited sensor, and
    (2) measuring radiation emitted by the excited sensor,
  (ii) measuring passage of time between at least two of the emission measurements to determine a time interval between identified emission measurement, and
  (iii) converting at least the identified emission measurements to a target-analyte concentration based upon a known conversion algorithm, and
(e) reporting at least one of (i) at least the two ascertained target-analyte concentrations and the time interval between those reported concentrations, and (ii) a rate of change in target-analyte concentration within the enclosed space calculated from data obtained in step (d).

In one embodiment, the space is hermetically enclosed, and the method further comprises the step of placing a liquid test sample into the space prior to hermetically enclosing the space.

In one embodiment, (i) the space is enclosed within a receptacle, (ii) a single probe is placed within the space, and (ii) the probe is contactlessly interrogated through the receptacle.

Preferably, the method is applied to achieve at least one of (i) a measurement of chemical activity of the test sample, (ii) a measurement of biological activity of the test sample, (iii) a presence/absence determination of a threshold concentration of aerobic microorganisms in the test sample, and (iv) an enumeration of aerobic microorganisms in the test sample at the time the test sample is placed in the space.

In one embodiment of the invention, there is provided a method for monitoring changes in target-analyte concentration within an enclosed space, comprising the steps of:
(a) obtaining an article of commerce as described above,
(b) dispensing a known number of probes from the container, constituting a fraction of the total number of commingled probes, into a space to form a sensor comprised of at least one probe,
(c) enclosing the space,
(d) ascertaining target-analyte concentration within the enclosed space over time by:
  (i) taking at least two emission measurements over time, each measurement comprising the steps of:
    (1) exposing the sensor to excitation radiation to create an excited sensor, and
    (2) measuring radiation emitted by the excited sensor,
  (ii) measuring passage of time between at least two of the emission measurements to determine a time interval between identified emission measurement, and
  (iii) converting at least the identified emission measurements to a target-analyte concentration based upon a known conversion algorithm, and
(e) reporting at least one of (i) at least two ascertained target-analyte concentrations and the time interval between those reported concentrations, and (ii) a rate of change in target-analyte concentration within the enclosed space calculated from data obtained in step (d).

In one embodiment of the invention, there is provided a method for measuring concentration of a target-analyte of interest within an enclosed space wherein the target-analyte of interest is selectable from and selectively transitional amongst a plurality of different target-analytes without accessing the space once enclosed, comprising the steps of:
(a) obtaining a supply of target-analyte sensitive probes as described above wherein the supply includes probes that are sensitive to different target-analytes and uniquely interrogatable relative to one another,
(b) placing at least two of the obtained probes sensitive to different target-analytes within a space, to form a sensor sensitive to at least two different target-analytes,
(c) enclosing the space, and
(d) ascertaining concentration of a target-analyte of interest within the enclosed space, selected from the at least two different target-analytes to which the at least two placed probes are sensitive, by:
  (i) exposing the sensor to excitation radiation effective for exciting the probe sensitive to the target-analyte of interest,
  (ii) measuring radiation emitted by the excited probe sensitive to the target-analyte of interest, and
  (iii) converting the measured emission to a concentration of the target-analyte of interest based upon a known conversion algorithm.

In one embodiment of the invention, there is provided a method for measuring concentration of at least two different target-analytes within an enclosed space, comprising the steps of:
  (a) obtaining a first supply of target-analyte sensitive probes as described above sensitive to a first target-analyte,
  (b) obtaining a second supply of target-analyte sensitive probes as described above sensitive to a second target-analyte which is different from the first target-analyte, wherein the probes sensitive to a first target-analyte and the probes sensitive to a second target-analyte are uniquely interrogatable relative to one another,
  (c) placing at least one probe from the first supply of probes and at least one probe from the second supply of probes within a space, to form a sensor sensitive to both first and second target-analytes,
  (d) enclosing the space,
  (e) ascertaining concentration of the first target-analyte within the enclosed space, by:
    (i) exposing the sensor to excitation radiation effective for exciting the probe sensitive to the first target-analyte,
    (ii) measuring radiation emitted by the excited probe sensitive to the first target-analyte, and
    (iii) converting the measured emission to a concentration of the first target-analyte based upon a known conversion algorithm, and
  (f) ascertaining concentration of the second target-analyte within the enclosed space, by:
    (i) exposing the sensor to excitation radiation effective for exciting the probe sensitive to the second target-analyte,
    (ii) measuring radiation emitted by the excited probe sensitive to the second target-analyte, and
    (iii) converting the measured emission to a concentration of the second target-analyte based upon a known conversion algorithm.

In one embodiment of the invention, there is provided a method for monitoring changes in concentration of at least two different target-analytes within an enclosed space, comprising the steps of:
  (a) obtaining a first supply of target-analyte sensitive probes as described above sensitive to a first target-analyte,
  (b) obtaining a second supply of target-analyte sensitive probes as described above sensitive to a second target-analyte which is different from the first target-analyte, wherein the probes sensitive to a first target-analyte and the probes sensitive to a second target-analyte are uniquely interrogatable relative to one another,
  (c) placing at least one probe from the first supply of probes and at least one probe from the second supply of probes within a space to form a sensor sensitive to both first and second target-analytes,
  (d) enclosing the space,
  (e) ascertaining concentration of the first target-analyte within the enclosed space over time by:
    (i) taking a first set of at least two emission measurements over time, each measurement comprising the steps of:
      (1) exposing the sensor to excitation radiation effective for exciting the probe sensitive to the first target-analyte, and
      (2) measuring radiation emitted by the excited probe sensitive to the first target-analyte,
    (ii) measuring passage of time between at least two of the first set emission measurements to determine a time interval between identified first set emission measurements, and
    (iii) converting at least the identified first set emission measurements to a concentration of the first target-analyte based upon a known conversion algorithm,
  (f) ascertaining concentration of the second target-analyte within the enclosed space over time by:
    (i) taking a second set of at least two emission measurements over time, each measurement comprising the steps of:
      (1) exposing the sensor to excitation radiation effective for exciting the probe sensitive to the second target-analyte, and
      (2) measuring radiation emitted by the excited probe sensitive to the second target-analyte,
    (ii) measuring passage of time between at least two of the second set emission measurements to determine a time interval between identified second set emission measurements, and
    (iii) converting at least the identified second set emission measurements to a concentration of the second target-analyte based upon a known conversion algorithm,
  (g) reporting at least one of (i) at least two ascertained first target-analyte concentrations and the time interval between those reported concentrations, and (ii) a rate of change in first target-analyte concentration within the enclosed space calculated from data obtained in step (e), and
  (h) reporting at least one of (i) at least two ascertained second target-analyte concentrations and the time interval between those reported concentrations, and (ii) a rate of change in second target-analyte concentration within the enclosed space calculated from data obtained in step (f).

In one embodiment of the invention, there is provided a method of preparing the probe according to the invention, which includes at least the steps of:
  (a) preparing a coating cocktail which contains at least the optically-active target-analyte sensitive material dissolved in a solvent,
  (b) applying the cocktail onto the porous scaffold particle, and
  (c) allowing the applied cocktail to dry, whereby a solid-state thin film coating of optically-active target-analyte sensitive material is formed on the scaffold particle to form the probe.

In one embodiment, the coating cocktail further includes a polymer operable for forming a target-analyte permeable polymer matrix when dried.

In one embodiment, the scaffold particle is soaked with the cocktail whereby the cocktail penetrates into and coats the pores in the scaffold particle, and the method further includes separating the coated scaffold particle from excess cocktail prior to drying.

DETAILED DESCRIPTION OF A PREFERRED EMBODIMENT

Definitions

As used herein, including the claims, the term "target-analyte" refers to a chemical substance, typically $O_2$, $CO_2$ or pH, capable of proportionally altering an optical property of an optically-active material containing a photoluminescent dye.

As used herein, including the claims, the term "contactless interrogation", means interrogation without tangible physical contact with the interrogated device, whereby interrogation can occur through an intervening bather.

As used herein, including the claims, the term "interrogation light" means electromagnetic radiation having a wavelength between 400 and 900 nm.

NOMENCLATURE

Probe
$10_{A1}$ Probe Sensitive to Target Analyte A1
$10_{A2}$ Probe Sensitive to Target Analyte A2
20 Scaffold Particle
29 Pores in Scaffold Particle
30 Target-Analyte Sensitive Coating
31 Target-Analyte-Sensitive Photoluminescent Dye
32 Target-Analyte-Permeable Polymer Matrix
40 Container for Supply of Probes
50 Assay Vessel
$50_1$ First Assay Vessel
$50_2$ Second Assay Vessel
50a Open Top of Assay Vessel
50b Bottom of Assay Vessel
59 Chamber of Assay Vessel
100 Supply of Probes
$100_1$ First Supply of Probes
$100_2$ Second Supply of Probes
200 Sensor
$200_1$ First Sensor
$200_2$ Second Sensor
A Target-Analyte
A1 First Target-Analyte
A2 Second Target-Analyte
S Test Sample

Description

Theory

The methods and compositions described herein are based on the quenching of an optical property, typically photoluminescence, by a target-analyte, typically oxygen ($O_2$). Luminescence encompasses both fluorescence and phosphorescence. Electromagnetic radiation in the ultraviolet or visible region is used to excite molecules to higher electronic energy levels. The excited molecules lose their excess energy by one of several methods. One of those methods is fluorescence. Fluorescence refers to the radiative transition of electrons from the first excited singlet state to the singlet ground state ($S_1$ to $S_0$). The lifetime of fluorescence is relatively short, approximately $10^{-9}$ to $10^{-7}$ seconds. However, intersystem crossing from the lowest excited singlet state to the triplet state often occurs and is attributed to the crossing of the potential energy curves of the two states. The triplet state so produced may return to the ground state by a radiative process known as phosphorescence. Phosphorescence is the radiative relaxation of an electron from the lowest excited triplet state to the singlet ground state ($T_1$ to $S_0$). Because the transition that leads to phosphorescence involves a change in spin multiplicity, it has a low probability and hence a relatively long lifetime of $10^{-4}$ to 10 seconds. Fluorescent and phosphorescent intensity and lifetime are known to change in a defined fashion relative to changes in the partial pressure of a target-analyte capable of quenching the photoluminescent molecules. Hence, the partial pressure of a target-analyte in fluid communication with a photoluminescent material can be determined by measuring photoluminescence intensity and/or lifetime.

Construction

A first aspect of the invention are probes 10 capable of reporting the partial pressure, and thereby the concentration, of a target-analyte A ($P_A$). The probes 10 are inexpensive, discrete, self-contained particles, which are remotely interrogatable by optical means and autonomously positionable, thereby permitting the probes 10 to be used for a wide variety of purposes and in combination with a wide variety of assay vessels to quickly, easily and reliably measure and monitor changes in analyte concentration in an environment. The probes 10 are particularly well suited for measuring and monitoring changes in target-analyte concentration in an enclosed environment in a non-invasive and non-destructive manner.

The probes 10 are sensitive to a target-analyte A, such as $O_2$, $CO_2$, CO or H. For purposes of simplicity only, and without intending to be limited thereto, the balance of the description shall reference $O_2$ as the target-analyte A since $O_2$-sensitive probes are the most commonly used types of optically active probes.

Figure 1:
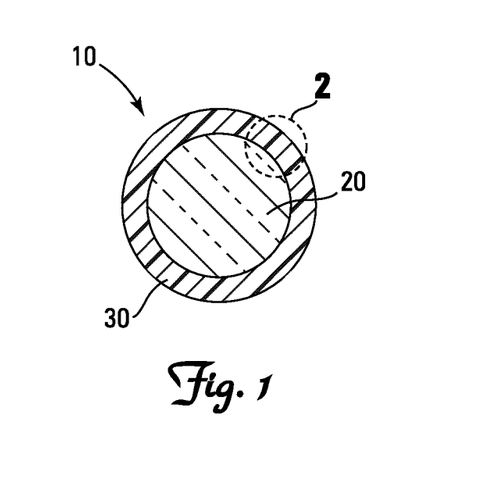
FIG. 1 is an enlarged, cross-sectional side-view of one embodiment of a probe according to the invention wherein the coated pores in the scaffold particle are not depicted and the coating of optically-active, target-analyte sensitive material is exaggerated to facilitate depiction of the coating.
Figure 2:
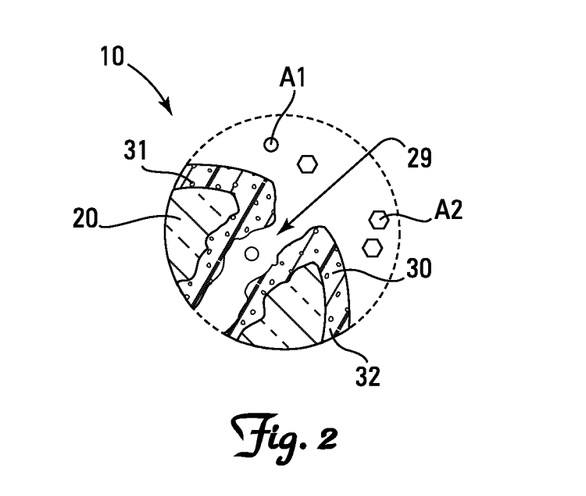
FIG. 2 is a grossly enlarged, cross-sectional side view of a surface portion of the probe depicted in FIG. 1.

Referring to FIGS. 1 and 2, the probes 10 each comprise a suitably sized porous scaffold particle 20 coated with a target-analyte A sensitive coating 30.

One of routine skill in the art is capable of selecting a suitable microporous scaffold particle 20 based upon the intended use of the probe 10, the target-analyte A of interest and the composition of the target-analyte sensitive coating 30. The porous scaffold particle 20 is preferably structurally stable, compatible with the solvent based target-analyte sensitive coating 30 during the coating process, and the dry coating 30, inert when used in accordance with its intended use, and exhibits excellent light scattering properties at the excitation and emission wavelengths for the target-analyte A sensitive coating 30. A nonexhaustive list of suitable materials for use as the porous scaffold particle 20 includes specifically, but not exclusively, glass, and polymers such as polyethylene, polypropylene, polytetrafluoroethylene, polystryrene, polycarbonate, polysulfone, polyvinyl chloride, cross-linked poly(styrene-divinylbenzene) and other similar co-polymers. Based upon its superior structural stability, coating compatability, and density, the preferred material is glass. The scaffold particle 20 is preferably constructed from a material which is translucent to interrogation light. The scaffold particle 20 is preferably a non-metalic, most preferably a nonferrous material, due to weight, cost and inability to provide sufficient porosity.

The scaffold particles 20 are preferably dry, homogeneous and non-aggregating. They may be in the form of beads, fibers, filaments, fines, pellets, powder, prills and the like.

Figure 3:
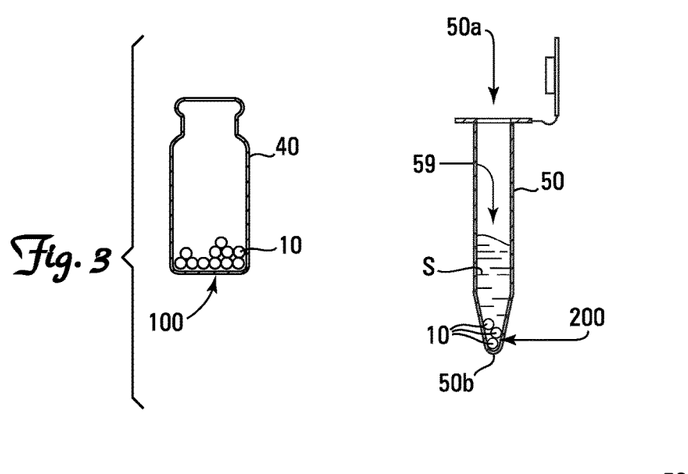
FIG. 3 is a schematic drawing of probes according to the invention employed to measure target-analyte in an assay vessel testing receptacle.

The scaffold particles 20 are preferably selected so that the resultant particulate probe 10 has a density of greater than 1.2 g/cm$^3$, most preferably a density of between 1.5 and 5 g/cm$^3$ so that the probe 10, when introduced into the chamber 59 of an assay vessel 50 through the open top 50$a$ of the vessel 50 will remain at or sink to the bottom 50$b$ of the vessel 50 when combined with common test sample materials S, thereby facilitating location and interrogation of the probe 10 within the assay vessel 50.

The target-analyte sensitive coating 30 is preferably includes a target-analyte-sensitive photoluminescent dye 31 embedded with a target-analyte A permeable polymer matrix 32.

One of routine skill in the art is capable of selecting a suitable indicator dye 31 based upon the target-analyte A of interest and the intended use of the probe 10. Preferred photoluminescent indicator dyes 31 are long-decay fluorescent or phosphorescent indicator dyes. For example, a nonexhaustive list of suitable $P_{O2}$ sensitive photoluminescent indicator dyes 31 includes specifically, but not exclusively, ruthenium(II)-bipyridyl and ruthenium(II)-diphenyl-phenanothroline complexes, porphyrin-ketones such as platinum(II)-octaethylporphine-ketone, platinum(II)-porphyrin such as platinum(II)-tetrakis(pentafluorophenyl)porphine, palladium(II)-porphyrin such as palladium(II)-tetrakis(pentafluorophenyl)porphine, phosphorescent metallocomplexes of tetrabenzoporphyrins, chlorins, azaporphyrins, and long-decay luminescent complexes of iridium(III) or osmium(II).

Typically and preferably, the target-analyte sensitive photoluminescent dye 31 is compounded with and embedded within a suitable target-analyte permeable polymer matrix 32. Again, one of routine skill in the art is capable of selecting a suitable polymeric matrix 32 based upon the target-analyte A of interest, the selected dye 31 and the intended use of the probe 10. For example, a nonexhaustive list of suitable polymers for use as the oxygen-permeable polymer matrix 32 includes specifically, but not exclusively, polystryrene, polycarbonate, polysulfone, polyvinyl chloride and some co-polymers.

The optically active particulate probe 10 preferably has at least one of a volume between 0.5 and 500 mm$^3$, preferably 5 to 100 mm$^3$, and a largest dimension of between 2 and 20 mm, preferably 3 to 10 mm. Probes 10 with a volume smaller than 0.5 mm$^3$ and/or a largest dimension of less than 2 mm are difficult to handle and accurately dispense, while probes 10 with a volume greater than 500 mm$^3$ and/or a largest dimension of greater than 20 mm are too large for use in many common testing receptacles 50, such as many traditional assay vessels, and unnecessarily increases the cost of each probe 10.

Manufacture and Supply

The optically active particulate probe 10 can be manufactured by any suitable technique. It is generally advantageous for the scaffold particle 20 to have a uniform size. The particle 20 may have a geometrical (e.g., planar, rectangular, spherical, oval, etc) or irregular shape and may have a rough or smooth exterior surface.

One technique is to dissolve or suspend the indicator dye 31, preferably with target-analyte permeable polymer 32, in a suitable organic solvent such as ethylacetate, immersing the porous scaffold particles 20 of the desired type, size and shape in the solution to coat the particles 20, including the pores 29, with dye 31, removing the coated particles 20, and allowing the coated particles 20 to dry. Alternatively, the solution may be sprayed onto the particles 20. Generally, the concentration of indicator dye 21 in the organic solvent should be in the range of 0.01 to 5% w/w. Generally, the concentration of the polymer 32 in the organic solvent should be in the range of 0.1 to 20% w/w, with the ratio of indicator dye 31 to polymer 32 in the range of 1:50 to 1:5,000 w/w.

Figure 5:
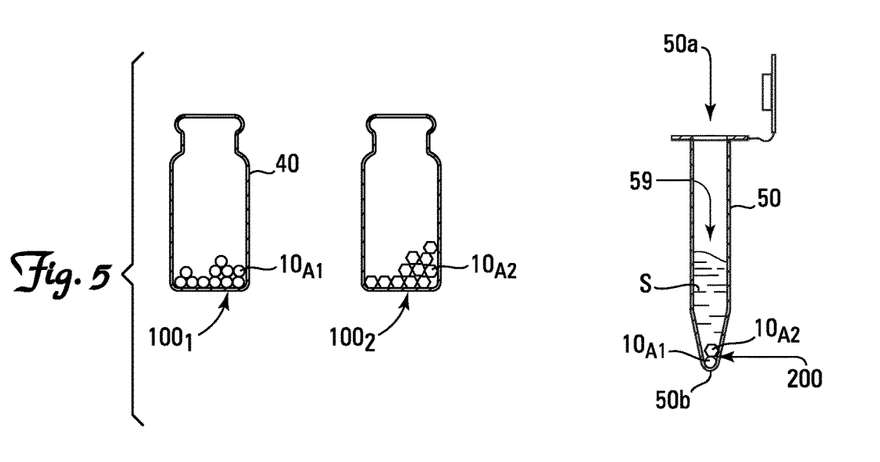
FIG. 5 is a schematic drawing of probes according to the invention, sorted by the target-analyte to which they are sensitive, employed to measure different target-analytes within the same assay vessel testing receptacle.
Figure 6:
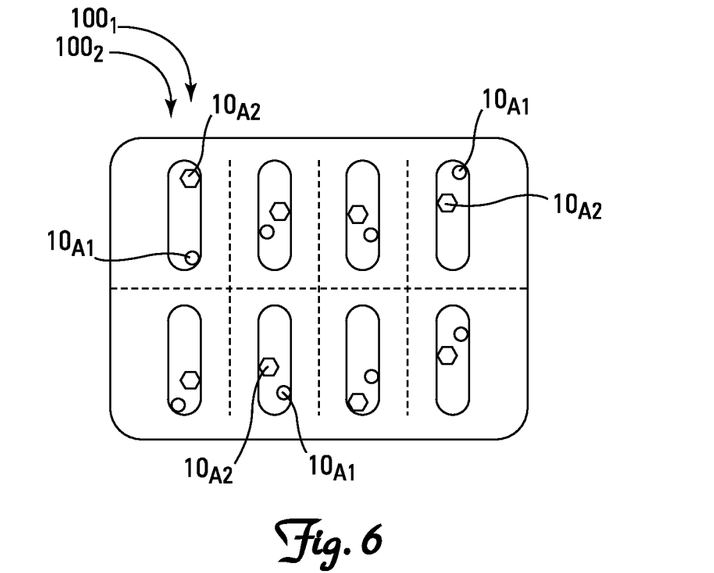
FIG. 6 is a top view of an alternative collated packaging of the sorted probes depicted in FIG. 5.

The probes 10 can be supplied as an article of commerce comprising a plurality of the probes 10, (e.g., 10 to 1,000 probes or more) retained as a commingled supply 100 of the probes 10 within a container 40 from which the probes 10 may be individually and discretely dispensed. Referring to FIGS. 5 and 6, when different probes 10 sensitive to different target-analytes A (e.g., probe $10_{A1}$ sensitive to target-analyte A1 and probe $10_{A2}$ sensitive to target-analyte A2) are to be placed into a testing receptacle such as an assay vessel 50, the supply $100_1$ and $100_2$ of each probe $10_{A1}$ and $10_{A2}$ may be sorted, as shown in FIG. 5, or collated as shown in FIG. 6.

The particulate probes 10 may be sanitized or sterilized before or after being deposited into the container 40 by any suitable means, such as heat, gamma irradiation or ethylene oxide, on order to avoid microbial contamination of a sample S undergoing microbial testing with the probes 10.

Use

Measuring Concentration of Single Target-Analyte A

Figure 4:
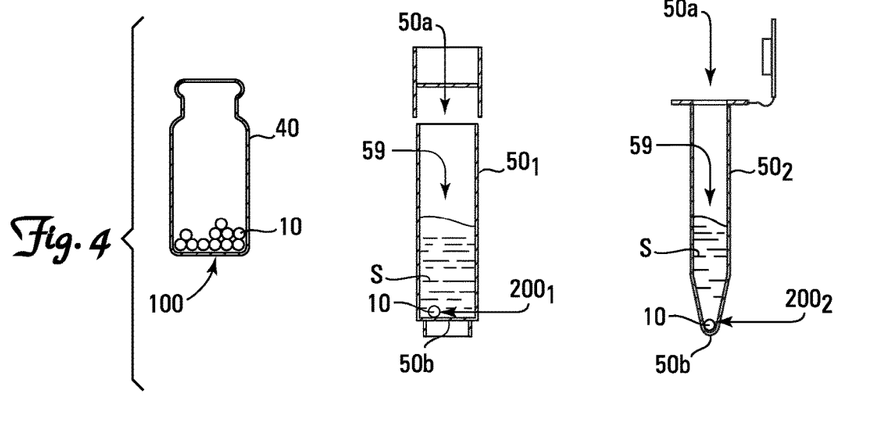
FIG. 4 is a schematic drawing probes according to the invention employed to measure target-analyte in multiple assay vessel testing receptacles.

Referring generally to FIGS. 3-5, the probe 10 can be used to quickly, easily, accurately and reliably measure the concentration of a target-analyte A in an environment (e.g., the sealed chamber 59 of an assay vessel 50 or the sealed chamber (not shown) of a package (not shown) containing a product (not shown) susceptible to spoilage or deterioration). The probe 10 can be interrogated in the same manner as typical target-analyte A sensitive photoluminescent probes are interrogated. Briefly, the probe 10 is used to measure the concentration of a target-analyte A in an environment by (A) placing the probe 10 into fluid communication with the environment to be monitored (e.g., within the sealed chamber 59 of an assay vessel 50 containing a test sample S) at a location where radiation at the excitation and emission wavelengths of the indicator dye 31 can be transmitted to and received from the probe 10 with minimal interference and without opening or otherwise breaching the integrity of the environment (e.g., without opening the assay vessel 50), (B) interrogating the probe 10 with an interrogation device (not shown), and (C) converting the measured emissions to a target-analyte A concentration within the environment based upon a known conversion algorithm or look-up table.

The radiation emitted by the excited probe 10 can be measured in terms of photoluminescence intensity, intensity ratio and/or lifetime (rate of decay, phase shift or anisotropy), with measurement of lifetime generally preferred as a more accurate and reliable measurement technique when seeking to establish the extent to which the indicator dye 31 has been quenched by target-analyte A.

Referring to FIG. 3, a preferred method of measuring the concentration of a target-analyte A within an enclosed space 59 employing a probe 10 includes the steps of (A) obtaining a supply 100 of the target-analyte sensitive probes 10, (B) placing a known number of probes 10 from the supply 100 of probes 10 within a space 59 to form a sensor 200 comprised of at least one probe 10, (C) enclosing the space 59, and (D) ascertaining target-analyte A concentration within the enclosed space 59 by: (i) exposing the sensor 200 to excitation radiation to create an excited sensor 200, (ii) measuring radiation emitted by the excited sensor 200, and (iii) converting the measured emission to a target-analyte A concentration based upon a known conversion algorithm.

Probes 10 are uniquely suited for measuring concentration of a target-analyte A within the chamber 59 of a plurality of dissimilar assay vessels 50. Referring to FIG. 4, the method includes the steps of (A) obtaining a supply 100 of probes 10 retained within a container 40, (B) dispensing a first known number of probes 10 from the container 40, constituting a first fraction of the total number of commingled probes 10, into a chamber 59 defined by a first assay vessel $50_1$ to form a first sensor $200_1$ comprised of at least one probe 10, (C) dispensing a second known number of probes 10 from the same container 40, constituting a second fraction of the total number of commingled probes 10, into the chamber 59 of a second assay vessel $50_2$ to form a second sensor $200_2$ comprised of at least one probe 10, wherein the second assay vessel $50_2$ is different than and dissimilar to the first r assay vessel $50_1$, (D) enclosing the chamber 59 defined by the first assay vessel $50_1$, (E) enclosing the chamber 59 defined by the second assay vessel $50_2$, (F) ascertaining target-analyte A concentration within the enclosed chamber 59 of the first assay vessel $50_1$ by: (i) exposing the first sensor $200_1$ to excitation radiation to create an excited first sensor $200_1$, (ii) measuring radiation emitted by the excited first sensor $200_1$, and (iii) converting the measured emission to a target-analyte A concentration based upon a known conversion algorithm, and (G) ascertaining target-analyte concentration within the enclosed chamber 59 of the second assay vessel $50_2$ by: (i) exposing the second sensor $200_2$ to excitation radiation to create an excited second sensor $200_2$, (ii) measuring radiation emitted by the excited second sensor $200_2$, and (iii) converting the measured emission to a target-analyte A concentration based upon a known conversion algorithm.

Monitoring Changes in Single Target-Analyte A Concentration

The probe 10 can also be used to quickly, easily, accurately and reliably monitor changes in target-analyte A concentration in an environment by (i) placing the probe 10 into fluid communication with the environment to be monitored at a location where radiation at the excitation and emission wavelengths of the indicator dye 31 can be transmitted to and received from the probe 10 with minimal interference and without opening or otherwise breaching the integrity of the environment, (B) ascertaining the target-analyte A concentration within the environment over time by (i) repeatedly exposing the probe 10 to excitation radiation over time, (ii) measuring radiation emitted by the excited probe 10 after at least some of the exposures, (iii) measuring passage of time during the repeated excitation exposures and emission measurements, and (iv) converting at least some of the measured emissions to a target-analyte A concentration based upon a known conversion algorithm, and (C) reporting at least one of (i) at least two ascertained target-analyte A concentrations and the time interval between those reported concentrations, and (ii) a rate of change in target-analyte A concentration within the environment calculated from data obtained in step (B). Conversion algorithms used to convert the measured emissions to a target-analyte concentration are well know to and readily developable by those with routine skill in the art.

Referring to FIG. 3, a preferred method for monitoring changes in target-analyte A concentration within an enclosed space 59 employing a probe 10 includes the steps of (A) obtaining a supply 100 of the probes 10, (B) placing a known number of probes 10 from the supply 100 of probes 10 within a space 59 to form a sensor 200 comprised of at least one probe 10, (C) enclosing the space 59, (D) ascertaining target-analyte A concentration within the enclosed space 59 over time by: (i) taking at least two emission measurements over time, each measurement comprising the steps of: (1) exposing the sensor 200 to excitation radiation to create an excited sensor 200, and (2) measuring radiation emitted by the excited sensor 200, (ii) measuring passage of time between at least two of the emission measurements to determine a time interval between identified emission measurements, and (iii) converting at least the identified emission measurements to a target-analyte A concentration based upon a known conversion algorithm, and (E) reporting at least one of (i) at least the two ascertained target-analyte concentrations and the time interval between those reported concentrations, and (ii) a rate of change in target-analyte A concentration within the enclosed space 59 calculated from data obtained in step (D).

Measuring Concentration of Deferrably Selectable Target-Analyte A

Probes 10 are also uniquely suited for measuring concentration of a target-analyte A of interest within an enclosed space 59 employing different probes 10 sensitive to different target-analytes A (e.g., probe $10_{A1}$ sensitive to target-analyte A1 and probe $10_{A2}$ sensitive to target-analyte A2), wherein the target-analyte A of interest is selectable from and selectively transitional amongst a plurality of different target-analytes A without accessing the space 59 once enclosed. The method includes the steps of (A) obtaining a supply 100 of probes 10 wherein the supply includes probes 10 that are sensitive to different target-analytes A (e.g., a supply $100_1$ of probes $10_{A1}$ sensitive to target-analyte A1 and a supply $100_2$ of probes $10_{A2}$ sensitive to target-analyte A2) and are uniquely interrogatable relative to one another, (B) placing at least two of the obtained probes 10 sensitive to different target-analytes A within a space 59, to form a sensor 200 sensitive to at least two different target-analytes A (e.g., target-analyte A1 and target-analyte A2), (C) enclosing the space 59, and (D) ascertaining concentration of a target-analyte A of interest within the enclosed space, selected from the at least two different target-analytes A to which the at least two placed probes 10 are sensitive (e.g., probe $10_{A1}$ sensitive to target-analyte A1 and probe $10_{A2}$ sensitive to target-analyte A2), by: (i) exposing the sensor 200 to excitation radiation effective for exciting the probe 10 sensitive to the target-analyte A of interest (e.g., probe $10_{A1}$ sensitive to target-analyte A1), (ii) measuring radiation emitted by the excited probe 10 sensitive to the target-analyte A of interest (e.g., probe $10_{A1}$ sensitive to target-analyte A1), and (iii) converting the measured emission to a concentration of the target-analyte A of interest (e.g., target-analyte A1) based upon a known conversion algorithm.

Measuring Concentration of Plurality of Different Target-Analytes A

Probes 10 are also uniquely suited for measuring the concentration of at least two different target-analytes A (e.g., target-analyte A1 and target-analyte A2) within an enclosed space 59 employing different target-analyte sensitive probes 10 (e.g., probe $10_{A1}$ sensitive to target-analyte A1 and probe $10_{A2}$ sensitive to target-analyte A2). The method includes the steps of (A) obtaining a first supply $100_1$ of target-analyte sensitive probes $10_{A1}$ which are sensitive to a first target-analyte A1, (B) obtaining a second supply $100_2$ of target-analyte sensitive probes $10_{A2}$ which are sensitive to a second target-analyte A2 which is different from the first target-analyte A1, and wherein the probes $10_{A1}$ sensitive to a first target-analyte A1 and the probes $10_{A2}$ sensitive to a second target-analyte A2 are uniquely interrogatable relative to one another, (C) placing at least one probe $10_{A1}$ from the first supply of probes $100_1$ and at least one probe $10_{A2}$ from the second supply of probes $100_2$ within a space 50, to form a sensor 200 sensitive to both first A1 and second A2 target-analytes, (D) enclosing the space 59, (E) ascertaining concentration of the first target-analyte A1 within the enclosed space 59, by: (i) exposing the sensor 200 to excitation radiation effective for exciting the probe $10_{A1}$ sensitive to the first target-analyte A1, (ii) measuring radiation emitted by the excited probe $10_{A1}$ sensitive to the first target-analyte A1, and (iii) converting the measured emission to a concentration of the first target-analyte A1 based upon a known conversion algorithm, and (F) ascertaining concentration of the second target-analyte A2 within the enclosed space 59, by: (i) exposing the sensor 200 to excitation radiation effective for exciting the probe $10_{A2}$ sensitive to the second target-analyte A2, (ii) measuring radiation emitted by the excited probe $10_{A2}$ sensitive to the second target-analyte A2, and (iii) converting the measured emission to a concentration of the second target-analyte A2 based upon a known conversion algorithm.

Monitoring Changes in Concentration of Multiple Target-Analytes A

Probes 10 are suited for simultaneously monitoring changes in the concentration of different target-analytes A of interest (e.g., target-analyte A1 and target-analyte A2) within an enclosed space 59. The method includes the steps of (A) obtaining a first supply $100_1$ of target-analyte sensitive probes $10_{A1}$ which are sensitive to a first target-analyte A1, (B) obtaining a second supply $100_2$ of target-analyte sensitive probes $10_{A2}$ which are sensitive to a second target-analyte A2 which is different from the first target-analyte A1, and wherein the probes $10_{A1}$ sensitive to a first target-analyte A1 and the probes $10_{A2}$ sensitive to a second target-analyte A2 are uniquely interrogatable relative to one another, (C) placing at least one probe $10_{A1}$ from the first supply of probes $100_1$ and at least one probe $10_{A2}$ from the second supply of probes $100_2$ within a space 59, to form a sensor 200 sensitive to both first A1 and second A2 target-analytes, (D) enclosing the space 59, (E) ascertaining concentration of the first target-analyte A1 within the enclosed space 59, by: (i) taking a first set of at least two emission measurements over time, each measurement comprising the steps of: (1) exposing the sensor 200 to excitation radiation effective for exciting the probe $10_{A1}$ sensitive to the first target-analyte, A1 and (2) measuring radiation emitted by the excited probe $10_{A1}$ sensitive to the first target-analyte A1, (ii) measuring passage of time between at least two of the first set emission measurements to determine a time interval between identified first set emission measurements, and (iii) converting the measured emission to a concentration of the first target-analyte based upon a known conversion algorithm, and (F) ascertaining concentration of the second target-analyte A2 within the enclosed space 59, by: (i) taking a second set of at least two emission measurements over time, each measurement comprising the steps of: (1) exposing the sensor 200 to excitation radiation effective for exciting the probe $10_{A2}$ sensitive to the second target-analyte A2, and (2) measuring radiation emitted by the excited probe $10_{A2}$ sensitive to the second target-analyte A2, (ii) measuring passage of time between at least two of the second set emission measurements to determine a time interval between identified second set emission measurements, and (iii) converting at least the identified second set emission measurements to a concentration of the second target-analyte based upon a known conversion algorithm, (G) reporting at least one of (i) at least two ascertained first target-analyte A1 concentrations and the time interval between those reported concentrations, and (ii) a rate of change in first target-analyte A1 concentration within the enclosed space 59 calculated from data obtained in step (E), and (H) reporting at least one of (i) at least two ascertained second target-analyte A2 concentrations and the time interval between those reported concentrations, and (ii) a rate of change in second target-analyte A2 concentration within the enclosed space 59 calculated from data obtained in step (F).

EXAMPLES

Example 1

(Manufacture of $O_2$ Particulate Probes)

The phosphorescent oxygen-sensitive dye platinum(II) benzoporphyrin was dissolved in a 5% solution of polystyrene in ethylacetate at a concentration of 1 mg platinum(II) benzoporphyrin/ml of solution to form a coating cocktail. 100 g of 4 mm diameter porous glass beads were soaked in the cocktail, separated on a mesh screen, dried on aluminum foil at room temperature for 2 hours, and placed into a container for future use.

Example 2

(Use of $O_2$ Particulate Probes to Detect Sample Sterility)

The probe produced according to Example 1 is transferred aseptically into a 15 ml sterile plastic vial with a screw cap. An aliquot of food or a medical sample, combined with a medium for supporting growth of microorganisms, is added aseptically to the vial along with the probe. The vial is capped and immediately thereafter the probe within the vial is externally interrogated with an Optech™ platinum external detector available from Mocon, Inc. to obtain an initial $t_0$ photoluminescence lifetime signal. The vial with its contents is incubated in an incubator at 30° C. for 24 hours, at which time the probe within the vial is again interrogated with the Optech™ platinum detector and an incubated $t_1$ photoluminescence lifetime signal measured. Any increase in the signal after incubation ($t_1-t_0$) indicates a proportional decrease in $O_2$ concentration within the vial as a result of the metabolic consumption of $O_2$ within the vial by microorganism introduced into the vial by the sample aliquot. A significant increase denotes that the sample aliquot as introduced into the vial was non-sterile, while a lack of any increase or a small increase denotes that the sample aliquot as introduced into the vial was sterile.

We claim:

1. A method for measuring concentration of a target-analyte within a sample in an enclosed space, comprising the steps of:
   (a) obtaining a supply of flexibly deployable, discrete, target-analyte sensitive probes comprising a porous scaffold particle coated with a coating material containing at least a fluorescent or phosphorescent indicator dye having a responsive optical characteristic that changes in response to changes in the concentration or partial pressure of target-analyte to which the coating material is exposed, wherein the scaffold particle is a bead having at least one of (i) a volume of 0.5 to 500 mm$^3$, and (ii) a largest dimension of 2 to 20 mm, (b) introducing into an enclosed space a fluidly dispensed known number of probes from the supply of probes and a sample, to form a test chamber containing a sensor comprised of at least one probe in intimate free-floating submerged physical contact with the sample, and (c) ascertaining target-analyte concentration within the sample by:
  (i) exposing the sensor to excitation radiation to create an excited sensor,
  (ii) measuring radiation emitted by the excited sensor, and
  (iii) converting the measured emission to a target-analyte concentration based upon a known conversion algorithm.

2. The method of claim 1, wherein the probes have a density of greater than 1.2 g/cm$^3$.

3. The method of claim 1, wherein (i) the responsive optical characteristic of the target-analyte sensitive coating material is at least one of photoluminescence lifetime and photoluminescence intensity, and (ii) the target-analyte sensitivity is sensitivity to the partial pressure of oxygen.

4. The method of claim 1 further comprising the step of enclosing the space to form a hermetically sealed test chamber, and (ii) the step of ascertaining target-analyte concentration within the sample comprises ascertaining target-analyte concentration within the sample without breaking the hermetic seal.

5. A method for measuring concentration of a target-analyte within an enclosed space containing an aliquot, comprising the steps of:

(a) obtaining an article of commerce comprising a plurality of probes retained as a commingled supply of probes within a container from which the probes may be individually and discretely fluidly dispensed, wherein the probes comprise a porous scaffold particle coated with a coating material containing at least a fluorescent or phosphorescent indicator dye having a responsive optical characteristic that changes in response to changes in the concentration or partial pressure of target-analyte to which the coating material is exposed, wherein the scaffold particle is a bead having at least one of (i) a volume of 0.5 to 500 mm$^3$, and (ii) a largest dimension of 2 to 20 mm, (b) introducing into a space a fluidly dispensed known number of probes from the container, constituting a fraction of the total number of commingled probes, and an aliquot to form a test chamber containing a sensor comprised of at least one probe in intimate free-floating physical contact with the aliquot, (c) enclosing the space to form a test chamber, and (d) ascertaining target-analyte concentration within the test chamber by:
  (i) exposing the sensor to excitation radiation to create an excited sensor,
  (ii) measuring radiation emitted by the excited sensor, and
  (iii) converting the measured emission to a target-analyte concentration based upon a known conversion algorithm.

6. The method of claim 5 wherein (i) the step of enclosing the space to form a test chamber comprises the step of hermetically sealing the space, and (ii) the step of ascertaining target-analyte concentration within the test chamber comprises ascertaining target-analyte concentration within the test chamber without breaking the hermetic seal.

7. A method for measuring concentration of a target-analyte within the chamber of a plurality of receptacles containing an aliquot, comprising the steps of:

(a) obtaining an article of commerce comprising a plurality of probes retained as a commingled supply of probes within a container from which the probes may be individually and discretely fluidly dispensed, wherein the probes comprise a porous scaffold particle coated with a coating material containing at least a fluorescent or phosphorescent indicator dye having a responsive optical characteristic that changes in response to changes in the concentration or partial pressure of target-analyte to which the coating material is exposed, wherein the scaffold particle is a bead having at least one of (i) a volume of 0.5 to 500 mm$^3$, and (ii) a largest dimension of 2 to 20 mm, (b) introducing into a first chamber defined by a first receptacle a fluidly dispensed first known number of probes from the container, constituting a first fraction of the total number of commingled probes, and a first aliquot to form a first chamber containing a first sensor comprised of at least one probe in intimate free-floating physical contact with the first aliquot, (c) introducing into a second chamber defined by a second receptacle a fluidly dispensed second known number of probes from the same container, constituting a second fraction of the total number of commingled probes, and a second aliquot to form a second chamber containing a second sensor comprised of at least one probe in intimate free-floating physical contact with the second aliquot, wherein the second receptacle is different than and dissimilar to the first receptacle, (d) enclosing the first chamber to form a first test chamber, (e) enclosing the second chamber to form a second test chamber, (f) ascertaining target-analyte concentration within the first test chamber by:
  (i) exposing the first sensor to excitation radiation to create an excited first sensor,
  (ii) measuring radiation emitted by the excited first sensor, and
  (iii) converting the measured emission to a target-analyte concentration based upon a known conversion algorithm, and (g) ascertaining target-analyte concentration within the second test chamber by:
  (i) exposing the second sensor to excitation radiation to create an excited second sensor,
  (ii) measuring radiation emitted by the excited second sensor, and
  (iii) converting the measured emission to a target-analyte concentration based upon a known conversion algorithm.

8. The method of claim 7 wherein (i) the step of enclosing the first chamber to form a first test chamber comprises the step of hermetically sealing the first chamber, (ii) the step of enclosing the second chamber to form a second test chamber comprises the step of hermetically sealing the second chamber, (iii) the step of ascertaining target-analyte concentration within the first test chamber comprises ascertaining target-analyte concentration within the first test chamber without breaking the hermetic seal, and (iv) the step of ascertaining target-analyte concentration within the second test chamber comprises ascertaining target-analyte concentration within the second test chamber without breaking the hermetic seal.

9. A method for monitoring changes in target-analyte concentration within an enclosed space containing an aliquot, comprising the steps of:
  (a) obtaining a supply of flexibly deployable, discrete, target-analyte sensitive probes comprising a porous scaffold particle coated with a coating material containing at least a fluorescent or phosphorescent indicator dye having a responsive optical characteristic that changes in response to changes in the concentration or partial pressure of target-analyte to which the coating material is exposed, wherein the scaffold particle is a bead having at least one of (i) a volume of 0.5 to 500 mm$^3$, and (ii) a largest dimension of 2 to 20 mm,
  (b) introducing into a space a fluidly dispensed known number of probes from the supply of probes and an aliquot, to form a test chamber containing a sensor comprised of at least one probe in intimate free-floating physical contact with the aliquot,
  (c) enclosing the space to form a test chamber,
  (d) ascertaining target-analyte concentration within the test chamber over time by:
    (i) taking at least two emission measurements over time, each measurement comprising the steps of:
      (1) exposing the sensor to excitation radiation to create an excited sensor, and
      (2) measuring radiation emitted by the excited sensor,
    (ii) measuring passage of time between at least two of the emission measurements to determine a time interval between identified emission measurement, and
    (iii) converting at least the identified emission measurements to a target-analyte concentration based upon a known conversion algorithm, and
  (e) reporting at least one of (i) at least the two ascertained target-analyte concentrations and the time interval between those reported concentrations, and (ii) a rate of change in target-analyte concentration within the test chamber calculated from data obtained in step (d).

10. The method of claim 9 wherein (i) the step of enclosing the space to form a test chamber comprises the step of hermetically sealing the space, and (ii) the step of ascertaining target-analyte concentration within the test chamber over time comprises ascertaining target-analyte concentration within the test chamber over time without breaking the hermetic seal during that time.

11. A method for monitoring changes in target-analyte concentration within a sample in an enclosed space, comprising the steps of:
  (a) obtaining an article of commerce comprising a plurality of probes retained as a commingled supply of probes within a container from which the probes may be individually and discretely fluidly dispensed, wherein the probes comprise a porous scaffold particle coated with a coating material containing at least a fluorescent or phosphorescent indicator dye having a responsive optical characteristic that changes in response to changes in the concentration or partial pressure of target-analyte to which the coating material is exposed, wherein the scaffold particle is a bead having at least one of (i) a volume of 0.5 to 500 mm$^3$, and (ii) a largest dimension of 2 to 20 mm,
  (b) introducing into an enclosed space a known number of probes from the container, constituting a fraction of the total number of commingled probes, and a sample to form a test chamber containing a sensor comprised of at least one probe in submerged intimate free-floating physical contact with the sample,
  (c) ascertaining target-analyte concentration within the sample over time by:
    (i) taking at least two emission measurements over time, each measurement comprising the steps of:
      (1) exposing the sensor to excitation radiation to create an excited sensor, and
      (2) measuring radiation emitted by the excited sensor,
    (ii) measuring passage of time between at least two of the emission measurements to determine a time interval between identified emission measurement, and
    (iii) converting at least the identified emission measurements to a target-analyte concentration based upon a known conversion algorithm, and
  (d) reporting at least one of (i) at least two ascertained target-analyte concentrations and the time interval between those reported concentrations, and (ii) a rate of change in target-analyte concentration within the sample calculated from data obtained in step (c).

12. The method of claim 11 wherein the step of enclosing the space to form a test chamber comprises the step of hermetically sealing the space, and (ii) the step of ascertaining target-analyte concentration within the test chamber over time comprises ascertaining target-analyte concentration within the test chamber over time without breaking the hermetic seal during that time.

13. A method for measuring concentration of a target-analyte of interest within an enclosed space containing an aliquot, wherein the target-analyte of interest is selectable from and selectively transitional amongst a plurality of different target-analytes without accessing the space once enclosed, comprising the steps of:
  (a) obtaining a supply of flexibly deployable, discrete, target-analyte sensitive probes comprising a porous scaffold particle coated with a coating material containing at least a fluorescent or phosphorescent indicator dye having a responsive optical characteristic that changes in response to changes in the concentration or partial pressure of target-analyte to which the coating material is exposed, wherein the scaffold particle is a microporous glass bead having at least one of (i) a volume of 0.5 to 500 mm$^3$, and (ii) a largest dimension of 2 to 20 mm wherein the supply includes probes that are sensitive to different target-analytes and uniquely interrogatable relative to one another,
  (b) introducing into a space at least two of the obtained probes sensitive to different target-analytes, and an aliquot to form a test chamber containing a sensor comprised of the at least two probes in intimate free-floating physical contact with the aliquot and sensitive to at least two different target-analytes,
  (c) enclosing the space to form a test chamber, and
  (d) ascertaining concentration of a target-analyte of interest within the test chamber, selected from the at least two different target-analytes to which the at least two probes are sensitive, by:
    (i) exposing the sensor to excitation radiation effective for exciting the probe sensitive to the target-analyte of interest,
    (ii) measuring radiation emitted by the excited probe sensitive to the target-analyte of interest, and (iii) converting the measured emission to a concentration of the target-analyte of interest based upon a known conversion algorithm.

14. The method of claim 13 wherein (i) the step of enclosing the space to form a test chamber comprises the step of hermetically sealing the space, and (ii) the step of ascertaining concentration of a target-analyte of interest within the test chamber comprises ascertaining concentration of a target-analyte of interest within the test chamber without breaking the hermetic seal.

* * * * *

UNITED STATES PATENT AND TRADEMARK OFFICE
CERTIFICATE OF CORRECTION

PATENT NO. : 9,945,778 B2
APPLICATION NO. : 14/649011
DATED : April 17, 2018
INVENTOR(S) : Papkovsky et al.

It is certified that error appears in the above-identified patent and that said Letters Patent is hereby corrected as shown below:

In the Specification

In Column 1, Line 49, delete "microtitter" and insert -- microtiter --, therefor.

In Column 1, Line 51, delete "Regensberg," and insert -- Regensburg, --, therefor.

In Column 1, Line 54, delete "PreSense." and insert -- PreSens. --, therefor.

In Column 2, Lines 29-30, delete "sensitive,d" and insert -- sensitive, --, therefor.

In Column 6, Line 4, delete "diphenylphenanotroline," and insert -- diphenylphenanthroline, --, therefor.

In Column 6, Line 10, delete "polystrene," and insert -- polystyrene, --, therefor.

In Column 11, Line 36, delete "bather." and insert -- barrier. --, therefor.

In Column 12, Line 47, delete "H." and insert -- $H^+$. --, therefor.

In Column 13, Line 2, delete "polystryrene," and insert -- polystyrene, --, therefor.

In Column 13, Line 5, delete "compatability," and insert -- compatibility, --, therefor.

In Column 13, Lines 8-9, delete "non-metalic," and insert -- non-metallic, --, therefor.

In Column 13, Line 23, delete "preferrably" and insert -- preferably --, therefor.

In Column 13, Lines 34-35, delete "diphenylphenanothroline" and insert -- diphenylphenanthroline --, therefor.

Signed and Sealed this
Twenty-fifth Day of August, 2020

Andrei Iancu
*Director of the United States Patent and Trademark Office*

CERTIFICATE OF CORRECTION (continued)
U.S. Pat. No. 9,945,778 B2

In Column 13, Line 52, delete "polystryrene," and insert -- polystyrene, --, therefor.

In Column 16, Line 4, delete "know" and insert -- known --, therefor.